US008922376B2

(12) United States Patent
Kangas et al.

(10) Patent No.: US 8,922,376 B2
(45) Date of Patent: Dec. 30, 2014

(54) CONTROLLING A USER ALERT

(75) Inventors: Jari Kangas, Tampere (FI); Leo Kärkkäinen, Helsinki (FI); Mikko Nurmi, Tampere (FI); Ville Ojanen, Espoo (FI); Ilkka Salminen, Tampere (FI); Sunil Sivadas, Tampere (FI); Akos Vetek, Helsinki (FI)

(73) Assignee: Nokia Corporation, Espoo (FI)

( * ) Notice: Subject to any disclaimer, the term of this patent is extended or adjusted under 35 U.S.C. 154(b) by 454 days.

(21) Appl. No.: 12/833,509

(22) Filed: Jul. 9, 2010

(65) Prior Publication Data

US 2012/0007740 A1    Jan. 12, 2012

(51) Int. Cl.
*G08B 21/00*    (2006.01)
*H04M 19/04*    (2006.01)
*H04M 1/725*    (2006.01)

(52) U.S. Cl.
CPC .......... *H04M 1/72569* (2013.01); *H04M 19/04* (2013.01)
USPC ..................... 340/573.1; 340/691.3; 340/540; 455/418; 455/567

(58) Field of Classification Search
USPC ............. 340/573.1, 691.3, 540; 455/418, 567
See application file for complete search history.

(56) References Cited

U.S. PATENT DOCUMENTS

| 4,228,806 A | 10/1980 | Lidow |
| 5,577,510 A | 11/1996 | Chittum et al. |
| 5,924,046 A * | 7/1999 | Martensson ................... 455/567 |
| 6,218,947 B1 | 4/2001 | Sutherland |
| 6,330,457 B1 * | 12/2001 | Yoon ........................... 455/550.1 |
| 7,016,705 B2 * | 3/2006 | Bahl et al. ...................... 455/566 |
| 7,542,379 B2 | 6/2009 | Kimel et al. |
| 2001/0014616 A1 * | 8/2001 | Matsuda et al. ............... 455/567 |
| 2002/0077534 A1 | 6/2002 | DuRousseau |
| 2003/0080872 A1 | 5/2003 | Gutta et al. |
| 2004/0209606 A1 | 10/2004 | Cleary et al. |
| 2005/0064916 A1 | 3/2005 | Ozluturk et al. |
| 2005/0190065 A1 | 9/2005 | Ronnholm |

(Continued)

FOREIGN PATENT DOCUMENTS

| EP | 0 694 283 A2 | 1/1996 |
| EP | 1 522 256 A1 | 4/2005 |

(Continued)

OTHER PUBLICATIONS

International Search Report and Written Opinion for International Application No. PCT/IB2011/052951, mailed Nov. 29, 2011.

(Continued)

*Primary Examiner* — Mohammad Ghayour
*Assistant Examiner* — Mark Rushing
(74) *Attorney, Agent, or Firm* — Alston & Bird LLP

(57) ABSTRACT

A method, apparatus and computer program are provided. The method comprises: performing a first detection of at least one bio-signal from at least one user; controlling a user output device to initiate a user alert, after performing the first detection of the at least one bio-signal; performing a second detection of the at least one bio-signal from the at least one user, after initiating the user alert; and processing the first detection of the at least one bio-signal and the second detection of the at least one bio-signal to determine whether one or more changes in the at least one bio-signal pass a significance test.

22 Claims, 5 Drawing Sheets

(56) References Cited

U.S. PATENT DOCUMENTS

| | | |
|---|---|---|
| 2006/0105817 A1* | 5/2006 | Naick et al. .................. 455/567 |
| 2006/0114222 A1 | 6/2006 | Araki et al. |
| 2007/0173733 A1 | 7/2007 | Le et al. |
| 2008/0157956 A1 | 7/2008 | Radivojevic et al. |
| 2009/0111446 A1* | 4/2009 | Cui et al. ..................... 455/418 |
| 2009/0134972 A1* | 5/2009 | Wu et al. ..................... 340/5.82 |
| 2009/0157325 A1 | 6/2009 | Jung et al. |
| 2009/0259138 A1 | 10/2009 | Lin et al. |
| 2010/0056226 A1* | 3/2010 | Bansal et al. ................ 455/567 |
| 2010/0090835 A1 | 4/2010 | Liu et al. |

FOREIGN PATENT DOCUMENTS

| | | |
|---|---|---|
| EP | 1 587 286 A2 | 10/2005 |
| EP | 1 867 274 A1 | 12/2007 |
| EP | 2 224 395 A1 | 9/2010 |
| JP | 2-034189 | 2/1990 |
| JP | 2000-268275 | 9/2000 |
| JP | 2003-018250 | 1/2003 |
| JP | 2004-049855 | 2/2004 |
| JP | 2004-305330 | 11/2004 |
| JP | 2005-151507 | 6/2005 |
| WO | WO 02/13672 A2 | 2/2002 |
| WO | WO 2004/012033 A2 | 2/2004 |
| WO | WO 2005/084538 A1 | 9/2005 |
| WO | WO 2006/090371 A2 | 8/2006 |
| WO | WO 2008/117145 A1 | 10/2008 |
| WO | WO 2009/033374 A1 | 3/2009 |
| WO | WO 2009/134205 A1 | 11/2009 |
| WO | WO 2011/027266 A1 | 3/2011 |

OTHER PUBLICATIONS

International Search Report and Written Opinion for International Application No. PCT/IB2011/052952, mailed Nov. 29, 2011.

Über Review; "Top Ten Most Annoying Alarm Clocks"; [Online]; [Retrieved on Jun. 24, 2011]; Retrieved from the Internet <URL: http://www.uberreview.com/2006/03/top-ten-most-annoying-alarm-clocks.htm.

iMusic vol. 3 (3 CD Set—Classical); [Online]; [Retrieved on Jun. 24, 2011]; Retrieved from the Internet <URL: http://www.luxevivant.com/index.asp?PageAction=VIEWPROD&ProdID=236.

Nokia Developer; Arto Holopainen's Blog; "Beyond iPhone: Symbian Device Human body control"; [Online]; [Retrieved on Jun. 24, 2011]; Retrieved from the Internet <URL: http://www.developer.nokia.com/Community/Blogs/blog/arto-holopainens-forum-nokia-blog/2007/08/19/beyond-iphone-symbian-device-human-body-control.

Ironic Sans: Idea: Motion-detecting cell phone ringer; [Online]; [Retrieved on Jun. 24, 2011]; Retrieved from the Internet <URL: http://www.ironicsans.com/2009/05/idea_motiondetecting_cell_phon.html.

Microsoft Research using EEG to "read minds in order to tag images" [Online]; [Retrieved on Jun. 24, 2011]; Retrieved from the Internet <URL: http://www.ditii.com/2010/01/20/microsoft-research-using-eeg-to-read-minds-in-order-to-tag-images/.

* cited by examiner

US 8,922,376 B2

CONTROLLING A USER ALERT

TECHNOLOGICAL FIELD

Embodiments of the present invention relate to controlling a user alert. In particular, they relate to controlling a user alert using detected bio-signals.

BACKGROUND

When an event occurs at a portable electronic device such as a mobile telephone, the portable electronic device may alert the user to the event. For example, a mobile telephone may provide an audible alert to inform the user that there is an incoming telephone call.

In some circumstances, a user may have become aware of the alert but be unable to switch off the alert. One example might be when a user is able to hear his telephone ringing while he is driving his car but he is unable to switch off the alert. This can be irritating for the user. Another example might be when a user is in a meeting and his telephone is out of reach.

BRIEF SUMMARY

According to some, but not necessarily all, embodiments of the invention there is provided a method, comprising: obtaining, from at least one detector, a first detection of at least one bio-signal from at least one user; controlling a user output device to initiate a user alert, after obtaining the first detection of the at least one bio-signal; obtaining, from the at least one detector, a second detection of the at least one bio-signal from the at least one user, wherein the second detection is performed after initiating the user alert; and processing the first detection of the at least one bio-signal and the second detection of the at least one bio-signal to determine whether one or more changes in the at least one bio-signal pass a significance test.

According to some, but not necessarily all, embodiments of the invention there is provided an apparatus, comprising: at least one memory storing a computer program comprising computer program instructions; and at least one processor configured to execute the computer program instructions to cause the apparatus at least to perform: obtaining, from at least one detector, a first detection of at least one bio-signal from at least one user; controlling a user output device to initiate a user alert, after obtaining the first detection of the at least one bio-signal; obtaining, from the at least one detector, a second detection of the at least one bio-signal from the at least one user, wherein the second detection is performed after initiating the user alert; and processing the first detection of the at least one bio-signal and the second detection of the at least one bio-signal to determine whether one or more changes in the at least one bio-signal pass a significance test.

According to some, but not necessarily all, embodiments of the invention there is provided an apparatus, comprising: means for obtaining, from at least one detector, a first detection of at least one bio-signal from at least one user; means for controlling a user output device to initiate a user alert, after obtaining the first detection of the at least one bio-signal; means for obtaining, from the at least one detector, a second detection of the at least one bio-signal from the at least one user, wherein the second detection is performed after initiating the user alert; and means for processing the first detection of the at least one bio-signal and the second detection of the at least one bio-signal to determine whether one or more changes in the at least one bio-signal pass a significance test.

According to some, but not necessarily all, embodiments of the invention there is provided a non-transitory computer readable medium comprising computer program instructions that, when executed by at least one processor, cause at least the following to be performed: obtaining, from at least one detector, a first detection of at least one bio-signal from at least one user; controlling a user output device to initiate a user alert, after obtaining the first detection of the at least one bio-signal; obtaining, from the at least one detector, a second detection of the at least one bio-signal from the at least one user, wherein the second detection is performed after initiating the user alert; and processing the first detection of the at least one bio-signal and the second detection of the at least one bio-signal to determine whether one or more changes in the at least one bio-signal pass a significance test.

BRIEF DESCRIPTION OF THE DRAWINGS

For a better understanding of various examples of embodiments of the present invention reference will now be made by way of example only to the accompanying drawings in which.

DETAILED DESCRIPTION

Figure 1:
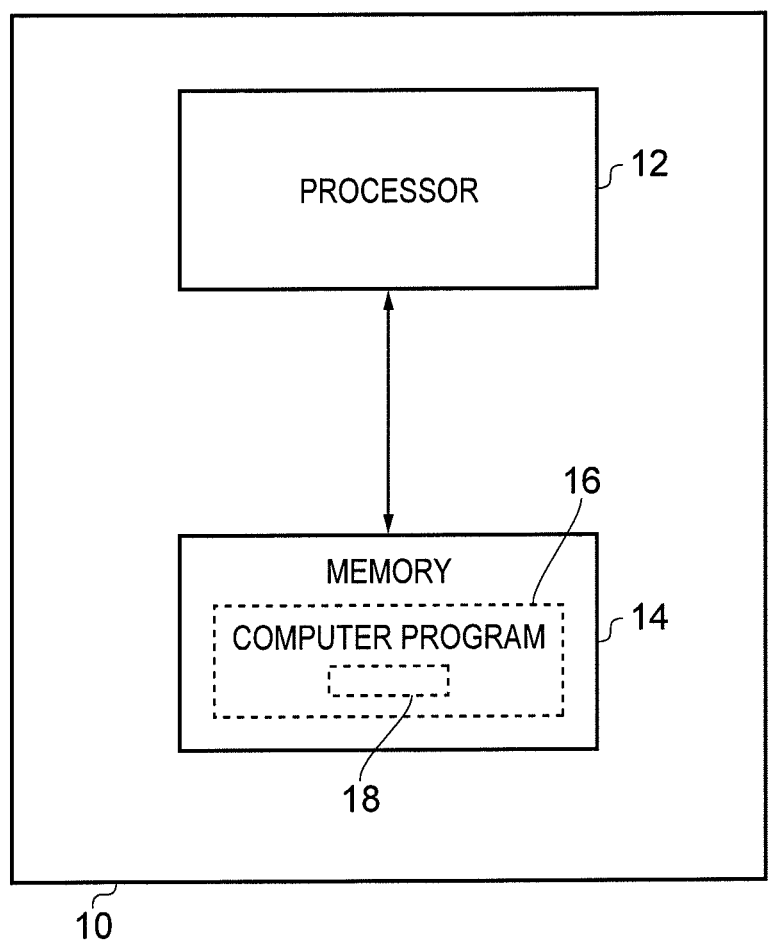
FIG. 1 illustrates an apparatus.

Embodiments of the invention relate to controlling a user alert using detected bio-signals. In particular, bio-signals are detected to determine whether a user has become aware of the user alert. If so, one or more characteristics of the user alert may be altered. For example, if the user alert is an audible alert, the user alert may be muted or the volume of the alert may be reduced.

The Figures illustrate an apparatus 10/20, comprising: at least one memory 14 storing a computer program 16 comprising computer program instructions 18; and at least one processor 12 configured to execute the computer program instructions 18 to cause the apparatus 10/20 at least to perform: obtaining, from at least one detector 26, a first detection of at least one bio-signal from at least one user; controlling a user output device 22 to initiate a user alert, after obtaining the first detection of the at least one bio-signal; obtaining, from the at least one detector 26, a second detection of the at least one bio-signal from the at least one user, wherein the second detection is performed after initiating the user alert; and processing the first detection of the at least one bio-signal and the second detection of the at least one bio-signal to determine whether one or more changes in the at least one bio-signal pass a significance test.

FIG. 1 illustrates an apparatus 10. The apparatus may, for example, be a chip or a chip-set. The apparatus 10 illustrated in FIG. 1 comprises a processor 12 and a memory 14. In alternative embodiments of the invention, the apparatus 10 may comprise multiple different processors and the functions of the processor 12 described below may be performed by the multiple different processors.

The processor 12 is configured to read from and write to the memory 14. The processor 12 may also comprise an output interface via which data and/or commands are output by the processor 12 and an input interface via which data and/or commands are input to the processor 12.

Although the memory 14 is illustrated as a single component, it may be implemented as one or more separate components, some or all of which may be integrated/removable and/or may provide permanent/semi-permanent/dynamic/cached storage.

The memory 14 stores a computer program 16 comprising computer program instructions 18 that control the operation of the apparatus 10/20 when loaded into the processor 12. The computer program instructions 18 provide the logic and routines that enables the apparatus 10/20 to perform the methods illustrated in FIGS. 3, 4 and 5. The processor 12, by reading the memory 14, is able to load and execute the computer program instructions 18.

The computer program 16 may arrive at the apparatus 10/20 via any suitable delivery mechanism 40. The delivery mechanism 40 may be, for example, a tangible, non-transitory computer-readable storage medium, a computer program, product, a memory device, a record medium such as a Compact Disc, a Digital Versatile Disc or Blu-Ray disc, or any article of manufacture that tangibly embodies the computer program 16. The delivery mechanism 40 may be a signal configured to reliably transfer the computer program 16.

Figure 2:
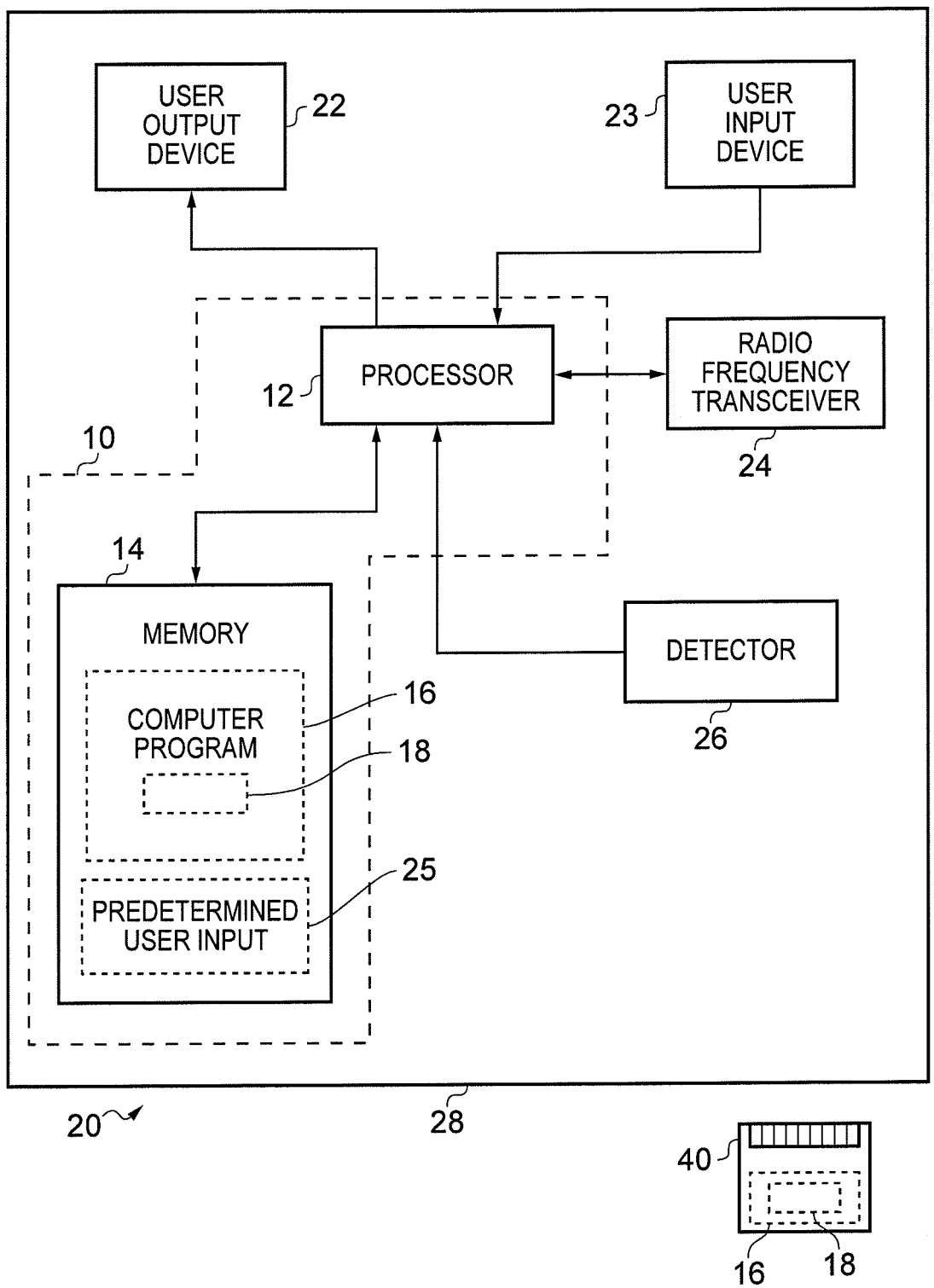
FIG. 2 illustrates a further apparatus.

FIG. 2 illustrates a further apparatus 20. The apparatus 20 illustrated in FIG. 2 may, for example, be a hand portable electronic device such as a mobile telephone, a personal music player, a personal digital assistant, a tablet computer, or a games console. The apparatus (hand portable electronic device) 20 may, for example, be wearable by a user. For example, the apparatus 20 may be wearable on a user's wrist or on a user's head. In other implementations of the invention, the apparatus 20 is not hand portable. For example, the apparatus may be an in-car system.

The apparatus 20 illustrated in FIG. 2 comprises the apparatus 10 illustrated in FIG. 1. In this particular example, the apparatus 20 further comprises a housing 28, a user output device 22, a user input device 23, a detector 26 and a radio frequency transceiver 24. For clarity reasons, only a single user output device 22, a single user input device 23, a single detector 26 and a single radio frequency transceiver 24 are illustrated in FIG. 2. However, in practice, the apparatus 10 may comprise multiple (different) user output devices, multiple (different) user input devices, multiple (different) detectors and/or multiple (different) radio frequency transceivers.

In this example, the housing 28 houses: the processor 12, the memory 14, the user output device 22, the user input device 23, the detector 26 and the radio frequency transceiver 24. The elements 12, 14, 22, 23, 24 and 26 are co-located within the housing 28. The elements 12, 14, 22, 23, 24 and 26 are operationally coupled and any number or combination of intervening elements can exist (including no intervening elements).

The processor 12 is configured to receive an input from the detector 26. While the detector 26 is housed within the housing 28 of the apparatus 20 in the FIG. 2 example, in other examples the detector 26 might not be housed within the housing 28 and might not be part of the apparatus 20. For example, the apparatus 20 may be a portable electronic device and the detector 26 may be in a counterpart device that is in communication with the portable electronic device (for example, via radio frequency signals). The counterpart device may, for instance, be wearable by a user (such as on a user's wrist, on a user's head or underneath a user's skin).

The detector 26 is configured to detect bio-signals. The detector 26 may be any type of detector that is suitable for detecting a bio-signal. A bio-signal is considered to be any type of signal that emanates from a biological being (such as a human being). A bio-signal may, for example, be a bio-electrical signal, a bio-mechanical signal, an aural signal, a chemical signal or an optical signal.

Bio-electrical signals may be electrical currents produced by one or more electrical potential differences across a tissue, organ or cell system such as the nervous system. Bio-electrical signals include signals that are detectable, for example, using electroencephalography, magnetoencephalography, galvanic skin response techniques, electrocardiography and electromyography.

Bio-mechanical signals may, for example, include signals that are detectable using one or more accelerometers or mechanomyography. Aural signals may, for example, include signals that are detectable using a microphone. Chemical signals may, for instance, include signals that are detectable using an oxygenation detector or a pH detector. Optical signals may, for example, include signals detectable using a camera.

The processor 12 is also configured to provide an output to the user output device 22 and to receive an input from the user input device 23. The user input device 23 may, for example, be a keypad or a microphone (in which case it may be the same device as the detector 26). The user output device 22 may, for example, be a display, a loudspeaker or a vibration alert device.

In some embodiments of the invention, the user input device 23 may be integrated with the user output device 22. For example, the user input device 23 and the user output device 22 may be provided by a touch sensitive display.

The processor 12 is configured to receive inputs from and provide outputs to the radio frequency transceiver 24. The radio frequency transceiver 24 is configured to transmit and receive radio frequency signals. The radio frequency transceiver 24 may, for example, be a cellular transceiver that is compatible with one or more cellular protocols such as GSM (Global System for Mobile Communications), IS-95 (Interim Standard 95) or UMTS (Universal Mobile Telecommunications System). Alternatively, the radio frequency transceiver 24 may be a short range transceiver that is compatible with one or more short range protocols, such as Bluetooth protocols or IEEE (Institute of Electrical and Electronic Engineers) protocols. In some embodiments of the invention, the apparatus 20 comprises one or more cellular transceivers and one or more short range transceivers.

Figure 3:
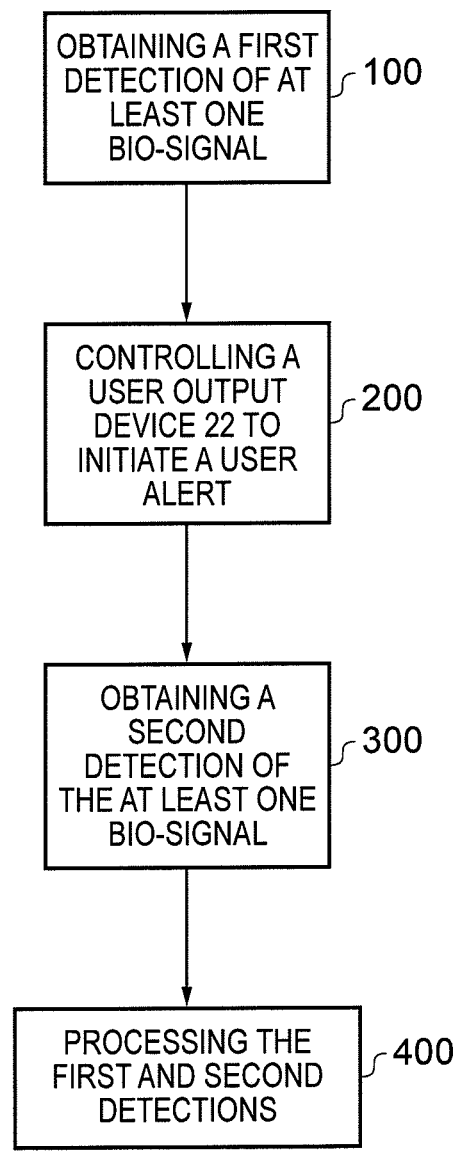
FIG. 3 illustrates a first method.

FIG. 3 illustrates a flow chart of a first method according to embodiments of the invention. In block 100 of FIG. 3, the processor 12 obtains a first detection, in the form of detection data, of at least one bio-signal from at least one detector 26. The first detection may be performed at an instance in time, or over a period of time (for example, depending upon on the type(s) of bio-signal(s) being detected). In some embodiments of the invention, the first detection may be obtained at several different instances in time or over several different periods of time.

The processor 12 may control the detector(s) 26 to obtain the first detection (for example, by activating the detector(s) 26). Alternatively, the processor 12 may obtain the first detection by merely reading the detector(s) 26 at one or more appropriate instances in time, or over one or more appropriate periods of time.

In some embodiments of the invention, the processor 12 is configured to obtain the first detection in response to the occurrence of an event at the apparatus 20. The event is associated with a user alert and may, for example, be an incoming communication from a third party, such as an incoming telephone call or message. Alternatively, the event may be a clock reaching a preset time. For example, a user may have programmed the apparatus 20 to provide a user alert at the preset time (for example, by setting an alarm clock or a reminder system).

Performing the first detection may comprise detecting one or more of any of the types of bio-signal described above. For example, one or more bio-electrical signals, one or more bio-mechanical signals, one or more aural signal signals, one or more chemical signals and/or one or more optical signals may be detected.

At block 200 in FIG. 3, after the first detection of one or more bio-signals has been obtained by the processor 12, the processor 12 controls one or more user output devices 22 to initiate a user alert. For example, the user alert may comprise one or more of the following: a visual alert, an aural alert and a vibratory alert. The purpose of the user alert is to get the user's attention. That is, to provide the user with information indicating that the event has occurred.

When the user becomes aware of the user alert, bio-signals originating at the user may change. Such changes may, for example, include the following:
(i) when the user notices the user alert he may move position, resulting in a change in the bio-mechanical and optical signals originating from the user;
(ii) the user may, for example, emit an aural signal upon seeing/hearing/feeling the user alert; and
(iii) bio-electrical signals produced by the user may change; for example, the user's skin may produce a galvanic skin response and the user's brain activity may change.

After initiation of the user alert, the detector(s) 26 perform a second detection of the one or more bio-signals that were detected at block 100. At block 300 in FIG. 3, the processor 12 obtains the second detection, in the form of detection data, of the one or more bio-signals. The second detection may be performed at an instance in time, or over a period of time (for example, depending upon on the type of bio-signal that is being detected). The processor 12 may control the detector(s) 26 to obtain the second detection (for example, by activating the detector(s) 26). Alternatively, the processor 12 may obtain the second detection by merely reading the detector(s) 26 at an appropriate instance in time, or over an appropriate period of time.

The changes that occur in the detected bio-signals after initiation of the user alert may indicate that the user has become aware of the user alert. At block 400 in FIG. 3, the processor 12 processes the first detection of the bio-signal(s) and the second detection of the bio-signal(s) to determine whether one or more changes in the detected bio-signal(s) pass a significance test. Passing the significance test indicates that at least one user has become aware of the user alert initiated at block 200.

In order to determine whether one or more changes in a bio-signal pass the significance test, the processor 12 may compare one or more values detected in the second detection with one or more values detected in the first detection. That is, rather than determining whether the second detection has a particular form by comparing the second detection with stored, predetermined data, the processor 12 may (merely) analyse whether an significant change has occurred in a bio-signal across a period of time that encompasses the initiation of the user alert.

For example, in order to determine whether a change in a bio-signal passes the significance test, the processor 12 may determine whether the magnitude of that change is above a threshold. Alternatively, if more than one bio-signal is being monitored, the processor 12 may determine whether the magnitudes of multiple changes are each above a threshold in order to determine whether the significance test is passed.

In some embodiments of the invention, after determining that the change(s) in the bio-signal(s) passes/pass the significance test, the processor 12 may alter at least one characteristic of the user alert initiated in block 200. For example, if the user alert comprises an aural alert, the processor 12 may mute the aural alert or reduce the volume of the aural alert. If the user alert comprises a visual alert displayed on a display, the processor 12 may remove the visual alert from display or reduce its prominence on the display. If the user alert comprises a vibratory alert, the processor 12 may control a vibration alert device to cease vibrating.

If the significance test is not passed, the processor 12 may escalate the user alert. For example, it may increase the volume of an audible alert or increase the prominence of a visual alert. Alternatively, the processor 12 may escalate the user alert by adding an audible alert to an existing visual alert, for example.

It may be that the change(s) in the bio-signal(s) which cause(s) the significance test to be passed and the user alert to be altered is/are not produced by the user with the intention of altering the user alert. For example, the change in the bio-signal(s) may be a reflex response from the user (such as a galvanic skin response) which causes the processor 12 to alter the user alert.

An advantage of embodiments of the invention is that user irritation is potentially minimised. For example, in some embodiments of the invention, the processor 12 may autonomously cease a user alert, or reduce an aspect of a user alert in magnitude or prominence in circumstances where it is not possible for the user to do so manually (for instance, when driving a car). Also, advantageously in embodiments of the invention, it is possible for the user alert to be initiated in a reasonably inconspicuous manner and for the user alert to be escalated over time (for example, in respect of an aural alert, increasing in volume) until the processor 12 determines that the user has noticed the user alert.

In some embodiments of the invention, the processor 12 may be configured to learn which change(s) in bio-signal(s) indicate(s) that a user has noticed a user alert and adapt or create a significance test accordingly. The learning process may be, for example, as follows. The processor 12 obtains a first detection of one or more bio-signals prior to the initiation of the user alert. The processor 12 then continues to monitor the bio-signal(s) and obtains a second detection after initiation of the user alert and just before the user deactivates the user alert manually (for example, by providing input at the user input device 23).

The change that occurs in a bio-signal between the first detection (obtained prior to initiation of the user alert) and the second detection (obtained after initiation of the user alert and just prior to manual deactivation of the user alert) can be considered to indicate that the user has noticed the user alert. The processor 12 may then adapt or create a significance test, for subsequent use, that tests whether the aforementioned change has been detected in order to determine whether to alter (for example, deactivate) a future user alert.

In some alternative embodiments of the invention, the processor 12 does not alter the user alert directly after determining that the change(s) in the bio-signal(s) passes/pass the significance test. For example, the processor 12 may require that the user provides a predetermined user input at the user input device 23 before the user alert is altered. Data identifying the predetermined user input may be stored in the memory 14 which enables the processor 12 to match a user input with the required input. This data is indicated in FIG. 2 by reference numeral 25.

For instance, consider an example in which the apparatus 20 is a portable electronic device with a user input device 23 in the form of an accelerometer. The processor 12 is configured to use the accelerometer to determine whether the user has tapped the portable electronic device with a digit. If the significance test is passed, the processor 12 enables the user to cease the user alert by tapping the portable electronic device with a digit. If the significance test is not passed, the processor 12 does not enable the user to cease the user alert by tapping the portable electronic device.

In this type of example, bio-signal detection and use of the significance test may advantageously reduce the possibility of the user alert being switched off inadvertently. This is because, if one or more bio-signal changes are not detected which indicate that the user has become aware of the user alert, it is not possible for the user to switch off the user alert by providing the predetermined user input. For instance, in the context of the above example, if the user does not notice the user alert and the device is inadvertently tapped by the user's leg while the device is in the user's pocket, the user alert will not be switched off.

In some further alternative embodiments of the invention, the significance test may form part of a two-part confidence test performed by the processor 12. When the processor 12 performs the confidence test, the significance test described above is performed and the processor 12 enables the user to provide user input to alter the user alert (possibly irrespective of the result of the significance test). The processor 12 decides, on the basis of the results of the significance test and a comparison between the user input received and a stored predetermined user input, whether or not to alter the user input.

For example, if the significance test is inconclusive and the comparison indicates that the received user input is a possible match (but not a good match) for the predetermined user input, the processor 12 may determine that the confidence test has not been passed. However, if the significant test had produced a more conclusive result (and therefore could be considered to have been 'passed'), the processor 12 may have determined that the confidence test had been passed.

In these embodiments of the invention, the change in the detected bio-signal(s) that is required to pass the significance test may vary depending upon the comparison between the received user input and the stored, predetermined user input.

Figure 4:
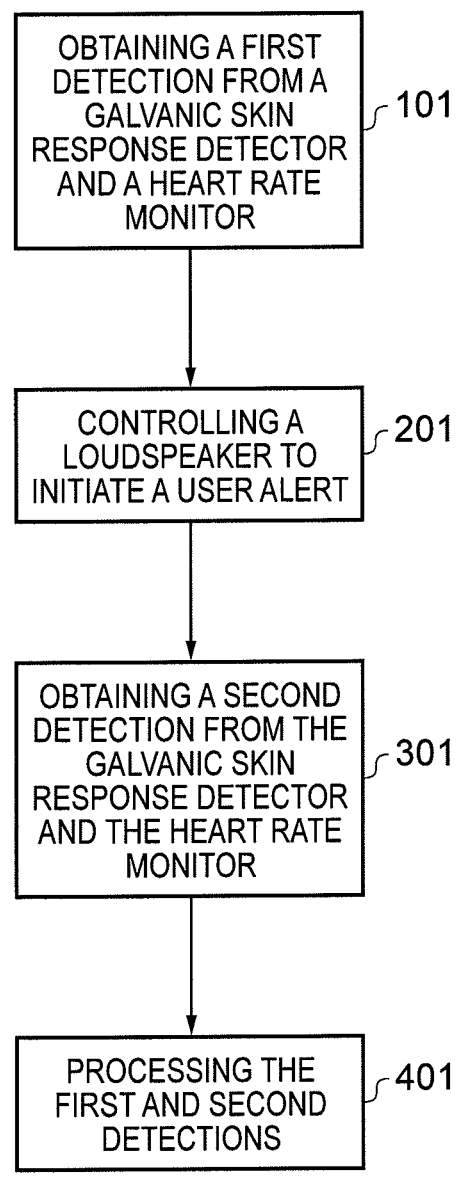
FIG. 4 illustrates a second method.

FIG. 4 illustrates a flow chart of a second method according to embodiments of the invention. In the second method, the apparatus 20 is a mobile telephone that is in radio communication with one or more counterpart devices comprising a galvanic skin response detector and a heart rate monitor.

The processor 12 determines, via a cellular transceiver of the mobile telephone, that there is an incoming telephone call. At block 101 in FIG. 4, the processor 12 responds to this event by obtaining a first detection of bio-signals from the galvanic skin response detector and the heart rate monitor.

At block 201 in FIG. 4, after obtaining the first detection of the bio-signals, the processor 12 controls a loudspeaker to initiate an audible user alert to alert the user to the telephone call.

At block 301 in FIG. 4, after initiating the user alert, the processor 12 obtains a second detection of bio-signals from the galvanic skin response detector and the heart rate monitor.

At block 401 in FIG. 4, the processor 12 processes the first and second detections to determine whether changes in the bio-signals pass a significance test. In some embodiments of the invention, in order to pass the significance test, the magnitude of the change in the bio-signal obtained from the galvanic skin response detector must be above a threshold and the magnitude of the change in the bio-signal obtained from the heart rate monitor must be above a threshold. In some alternative embodiments of the invention, in order to pass the significance test, the change in the bio-signal obtained from the galvanic skin response detector must be above a threshold or, alternatively, the magnitude of the change in the bio-signal obtained from the heart rate monitor must be above a threshold.

Passing the significance test indicates that the user has become aware of the user alert. If the significance test is passed, the processor 12 may control the loudspeaker to reduce the volume of the user alert or it may mute (silence) the user alert. If the significance test is not passed, the processor 12 may control the loudspeaker to increase the volume of the user alert to try to get the user's attention.

Figure 5:
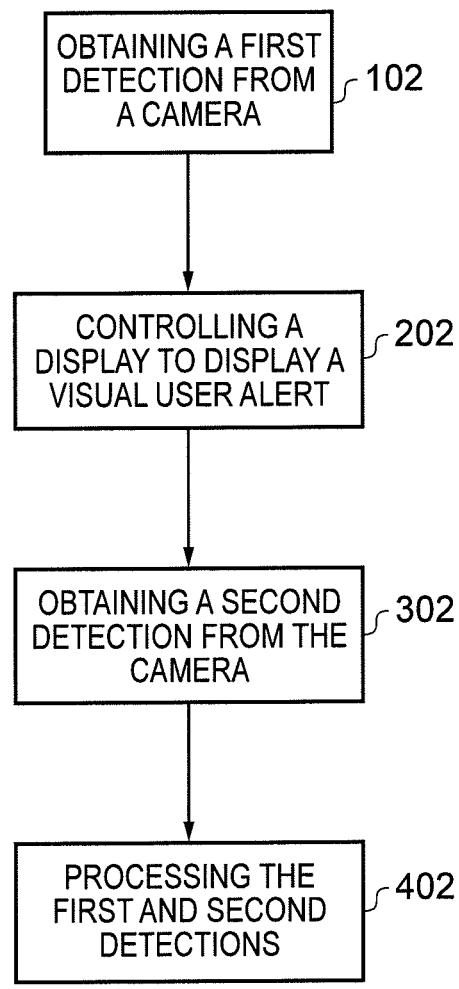
FIG. 5 illustrates a third method.

FIG. 5 illustrates a flow chart of a third method according to embodiments of the invention. In the third method, the apparatus 20 is a personal computer connected to a network. The personal computer comprises a display and a camera.

The camera of the personal computer is directed towards a group of users. The users may, for example, be seated. The processor 12 determines that a message is about to be received via the network. At block 102 in FIG. 5, the processor 12 responds to this event by obtaining a first detection of a bio-signal from the camera. The first detection may, for example, be a still image or a video of the users.

At block 202 in FIG. 5, after obtaining the first detection of the bio-signal, the processor 12 controls the display to display a visual user alert to alert the users to the message.

At block 302 in FIG. 5, after controlling the display to display the visual user alert, the processor 12 obtains a second detection of the bio-signal from the camera. The second detection may, for example, be a still image or a video of the users.

At block 402 in FIG. 5, the processor 12 processes the first and second detections of the bio-signal to determine whether one or more changes in the bio-signal pass a significance test. For example, if the first and second detections are still images or videos of the users, the processor 12 may compare the first detection with the second detection to determine whether a user, from the group of users, responded to the visual user alert.

For instance, the processor 12 may determine that the significance test is passed if it compares the first and second detections and determines from the comparison that at least one user, from the group of users, got up from his/her seat and came over to view the display more closely after the visual user alert was initiated.

The processor 12 may determine that the significance test is not passed if it compares the first and second detections and determines from the comparison that none of the users have noticed the visual user alert. For example, it may determine that from the comparison that nobody and has got up from his/her seat to view the display more closely after the visual alert was initiated.

References to 'computer-readable storage medium', 'computer program product', 'tangibly embodied computer program' etc. or a 'controller', 'computer', 'processor' etc. should be understood to encompass not only computers having different architectures such as single/multi-processor architectures and sequential (Von Neumann)/parallel architectures but also specialized circuits such as field-programmable gate arrays (FPGA), application specific circuits (ASIC), signal processing devices and other processing circuitry. References to computer program, instructions, code etc. should be understood to encompass software for a programmable processor or firmware such as, for example, the programmable content of a hardware device whether instructions for a processor, or configuration settings for a fixed-function device, gate array or programmable logic device etc.

As used in this application, the term 'circuitry' refers to all of the following:
(a) hardware-only circuit implementations (such as implementations in only analog and/or digital circuitry); and
(b) to combinations of circuits and software (and/or firmware), such as (as applicable): (i) to a combination of processor(s) or (ii) to portions of processor(s)/software (including digital signal processor(s)), software; and memory(ies) that work together to cause an apparatus, such as a mobile telephone or server, to perform various functions); and
(c) to circuits, such as a microprocessor(s) or a portion of a microprocessor(s), that require software or firmware for operation, even if the software or firmware is not physically present.

This definition of 'circuitry' applies to all uses of this term in this application, including, in any claims. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular claim element, a baseband integrated circuit or applications processor integrated circuit for a mobile telephone or a similar integrated circuit in a server, a cellular network device, or other network device.

The blocks illustrated in the FIGS. 3, 4 and 5 may represent operations in a method and/or sections of code in the computer program 16. The illustration of a particular order to the blocks does not necessarily imply that there is a required or preferred order for the blocks and the order and arrangement of the blocks may be varied. Furthermore, it may be possible for some blocks to be omitted.

Although embodiments of the present invention have been described in the preceding paragraphs with reference to various examples, it should be appreciated that modifications to the examples given can be made without departing from the scope of the invention as claimed. For example, some examples of embodiments of the invention are described in relation to FIGS. 4 and 5. In these examples, the detector(s) 26 detecting the bio-signals are described as being a camera, a galvanic skin response detector and a heart rate monitor. However, it will be appreciated that by those skilled in the art that, in other embodiments of the invention, other types of detector may be used for detecting other types of bio-signal.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. A method, comprising:
   obtaining, from at least one detector, a first detection of at least one bio-signal from at least one user;
   controlling a user output device to initiate a user alert, after obtaining the first detection of the at least one bio-signal;
   obtaining, from the at least one detector, a second detection of the at least one bio-signal from the at least one user, wherein the second detection is performed after initiating the user alert;
   determining whether the at least one bio-signal has changed in a manner so as to satisfy a significance test from prior to the user alert to following the user alert;
   receiving a user input to alter the user alert;
   comparing the user input to a stored predetermined user input; and
   varying a required change in the at least one bio-signal needed to satisfy the significance test, based on the comparison of the user input to the stored predetermined user input.

2. A method as claimed in claim 1, wherein passing the significance test indicates that at least one user has become aware of the user alert.

3. A method as claimed in claim 1, wherein determining whether one or more changes in the at least one bio-signal pass a significance test comprises determining whether the magnitude of at least one change is above a threshold.

4. A method as claimed in claim 1, further comprising: in response to at least one of determining that one or more changes in the at least one bio-signal pass the significance test, or determining the user input matches the stored predetermine user input, altering at least one characteristic of the user alert.

5. A method as claimed in claim 1, wherein the user alert comprises a visual, aural or vibratory alert for getting the user's attention.

6. A method as claimed in claim 1, wherein the user alert is for alerting the user to an event that has occurred at a hand portable electronic device.

7. A method as claimed in claim 6, wherein the event is an incoming communication from a remote party, or reaching a preset time.

8. The method according to claim 1, wherein the first detection of the at least one bio-signal comprises an indication of no movement of a device, and the second detection of the at least one bio-signal comprises an indication of movement.

9. The method according to claim 1, wherein the first detection of the at least one bio-signal comprises an indication of no user contact with a device, and the second detection of the at least one bio-signal comprises an indication of user contact with the device.

10. The method according to claim 1, wherein the first detection of the at least one bio-signal comprises an indication of no voice being detected, and the second detection of the at least one bio-signal comprises a voice being detected.

11. The method according to claim 1, further comprising:
   in response to the comparison of the user input to the stored predetermined user input, disregarding the significance test.

12. The method according to claim 1, further comprising:
   determining if the significance is satisfied based on the varied required change in the at least one bio-signal needed to satisfy the significance test.

13. The method according to claim 1, wherein varying the required change of the at least one bio-signal needed to satisfy the significance test comprises increasing a threshold measure of change.

14. An apparatus, comprising:
   at least one memory storing a computer program comprising computer program instructions; and at least one processor configured to execute the computer program instructions to cause the apparatus at least to perform:

obtaining, from at least one detector, a first detection of at least one bio-signal from at least one user;

controlling a user output device to initiate a user alert, after obtaining the first detection of the at least one bio-signal;

obtaining, from the at least one detector, a second detection of the at least one bio-signal from the at least one user, wherein the second detection is performed after initiating the user alert;

determining whether the at least one bio-signal has changed in a manner so as to satisfy a significance test from prior to the user alert to following the user alert;

receiving a user input to alter the user alert;

comparing the user input to a stored predetermined user input; and varying a required change in the at least one bio-signal needed to satisfy the significance test, based on the comparison of the user input to the stored predetermined user input.

15. An apparatus as claimed in claim 14, wherein passing the significance test indicates that at least one user has become aware of the user alert.

16. An apparatus as claimed in claim 14, wherein determining whether one or more changes in the at least one bio-signal pass a significance test comprises determining whether the magnitude of at least one change is above a threshold.

17. An apparatus as claimed in claim 14, wherein the at least one processor is configured to execute the computer program instructions to cause the apparatus to perform: in response to at least one of determining that one or more changes in the at least one bio-signal pass the significance test, or determining the user input matches the stored predetermined user input, altering at least one characteristic of the user alert.

18. An apparatus as claimed in claim 14, wherein the user alert comprises a visual, audible or vibratory alert for getting the user's attention.

19. An apparatus as claimed in claim 14, wherein the user alert is for alerting the user to an event that has occurred at a hand portable electronic device.

20. A non-transitory computer readable medium comprising computer program instructions that, when executed by at least one processor, cause at least the following to be performed:

obtaining, from at least one detector, a first detection of at least one bio-signal from at least one user;

controlling a user output device to initiate a user alert, after obtaining the first detection of the at least one bio-signal;

obtaining, from the at least one detector, a second detection of the at least one bio-signal from the at least one user, wherein the second detection is performed after initiating the user alert;

determining whether the at least one bio-signal has changed in a manner so as to satisfy a significance test from prior to the user alert to following the user alert;

receiving a user input to alter the user alert;

comparing the user input to a stored predetermined user input; and varying a required change in the at least one bio-signal needed to satisfy the significance test, based on the comparison of the user input to the stored predetermined user input.

21. A non-transitory computer readable medium as claimed in claim 20, wherein passing the significance test indicates that at least one user has become aware of the user alert.

22. A non-transitory computer readable medium as claimed in claim 20, wherein determining whether one or more changes in the at least one bio-signal pass a significance test comprises determining whether the magnitude of at least one change is above a threshold.

* * * * *